United States Patent [19]
Bernard et al.

[11] Patent Number: 5,279,958
[45] Date of Patent: Jan. 18, 1994

[54] SURFACE PROTEIN OF BASAL EPIDERMAL CELLS, ANTIBODIES CAPABLE OF RECOGNIZING SAID PROTEIN, AND THEIR USE, AND HYBRID CELLULAR STOCKS CAPABLE OF SECRETING SUCH ANTIBODIES

[75] Inventors: Bruno Bernard; Yves Darmon, both of Antibes, France

[73] Assignee: Dermatologiques (CIRD), Valbonne, France

[21] Appl. No.: 114,947

[22] Filed: Oct. 30, 1987

[30] Foreign Application Priority Data

Oct. 31, 1986 [FR] France ............ 86 15208

[51] Int. Cl.$^5$ ............ C07K 15/28; C07K 17/00; C07K 15/14; C12N 5/12
[52] U.S. Cl. ............ 435/240.27; 530/388.2; 530/389.7; 530/391.1; 530/391.3; 530/395; 530/806
[58] Field of Search ............ 530/350, 395, 387, 806, 530/388.2, 389.7, 391.1, 391.3; 435/240.1, 240.2, 240.27; 436/501

[56] References Cited

U.S. PATENT DOCUMENTS 4,837,306 6/1989 Ling et al. ............ 530/388.2
4,996,298 2/1991 Salem et al. ............ 530/395

FOREIGN PATENT DOCUMENTS 141079 5/1985 European Pat. Off.
157613 10/1985 European Pat. Off.
163303 12/1985 European Pat. Off.
163304 12/1985 European Pat. Off.
WO85/03132 7/1985 PCT Int'l Appl.

OTHER PUBLICATIONS

Darmon et al. 1987. Pharmacol. Shim. 1:10–21.
Stanley et al. 1986. J. Immunol. 136(4):1227–1230, (abstract).
Scnmelz et al. 1986. Eur. J. Cell Biol. 42(2):184–199, (abstract).
Strefling et al. 1985. J. Invert. Dermatol. 84(2): 100–104 (abstract).
Zambruno et al. 1986. Acta Derm Venereol. 66(3):185–192, (abstract).
Viac et al. 1985. Pathol. Res. Pract. 180(6): 577–583, (abstract).
Gottlieb et al. 1985. J. Am. Acad. Dermatol. 13(1):54–65, (abstract).
Gusterson et al. 1985. Differentiation 30(2):102–110, (abstract).
Chemical Abstracts, vol. 105, No. 11, Sep. 1986, p. 480, No. 95671t B. A. Bernard.
Chemical Abstracts, vol. 105, No. 7, Aug. 1986, p. 411, No. 58395k, King et al.
Chemical Abstracts, vol. 105, No. 7, Aug. 1986, p. 438, No. 58657x, Ma et al.
Cancer Research, vol. 45, Feb. 1985, pp. 783, 790; Hamburger et al "Isolation and characterization of a monoclonal antibody specific for epithelial cells".
Biological Abstracts, vol. 80, No. 1, Jul. 1985, No. 4165, Viac et al.
Proc. Natl. Acad. Sci. USA, vol. 83, No. 19, Oct. 1986, pp. 7282–7286, Jones et al.
Proc. Natl. Acad. Sci. USA, vol. 83, No. 8, Apr. 1986, pp. 2657–2661, Parrish et al.
Chemical Abstracts, vol. 100, No. 21, May 1984, p. 453, No. 172635k, Weiss et al.
Biological Abstracts, vol. 78, No. 8, Aug. 1984, No. 60667, Murphy et al.

*Primary Examiner*—Keith C. Furman
*Attorney, Agent, or Firm*—Cushman, Darby & Cushman

[57] ABSTRACT

A protein characterized by the fact that it is a non-keratinic protein present on the apicolateral surface and absent on the basal surface of basal epidermal cells, in particular in man, that it is present in a nonpolarized manner in basocellular and spinocellular carcinomas and absent in melanoma and naevus cells; antibodies directed against said protein, their preparation and their use as reagents; cellular stocks secreting such antibodies, and their preparation.

7 Claims, No Drawings

SURFACE PROTEIN OF BASAL EPIDERMAL CELLS, ANTIBODIES CAPABLE OF RECOGNIZING SAID PROTEIN, AND THEIR USE, AND HYBRID CELLULAR STOCKS CAPABLE OF SECRETING SUCH ANTIBODIES

The present invention relates to a protein present on the surface of the basal cells of the normal human epidermis, to antibodies, which are capable of recognizing an antigen site of said protein, to their preparation and to their use, in particular, as reagents for the study of the normal or pathological differentiation of the cells of the epidermis.

It is known that the epidermis contains a basal membrane on which rests a layer of proliferative basal cells and suprabasal layers of cells in the process of differentiation which are progressively keratinized and finished by forming on the surface of the skin a corneal layer of completely keratinized dead cells. All these cells are constantly renewed from the proliferative basal layer.

In order to study skin diseases (for example, psoriasis, warts, papilloma, cancers, etc.), it is necessary to have a better understanding of the differentiation between normal and malignant epidermal cells, which are further called keratinocytes.

For example, it is not presently known if psoriasis is caused by an excessive proliferation of cells of the basal membrane, such as the cells which did not have time to be differentiated (in other words, the differentiation stopped at a certain stage) or indeed if it is caused by a differentiation of diseased cells other than that of the normal cells.

In order to carry out such studies, it is important to have different markers for the differentiation of the keratinocytes.

The present invention relates to such markers, to their preparation and to their use.

In particular, the present invention relates to a new protein, characterized by the fact:

that it is a nonkeratinic protein present on the apicolateral surface and absent on the basal surface of basal epidermal cells, in particular in man, monkey, horse, cow, goat and guinea pig, including psoriasic and papillomatous basal cells;

that it is absent from the surface of the basal epidermal cells of the rabbit and the mouse;

that it is present in the following epithelial tissues of man (in addition to the skin): esophagus, ureter, and, to a lesser degree, stomach, colon and small intestine;

that it is present, in a nonpolarized manner, on the following pathological cells: basocellular carcinoma, spinocellular carcinoma, and absent on the melanoma and naevus cells; and that it is recognized by the antibody secreted by the hybrid cellular stock BC$_2$ deposited on Oct. 27, 1986, in the National Collection of Microorganisms of the Pasteur Institute under the No. I-614 the address of the Pasteur Institute being 25 rue du Docteur Roux, 75724 Paris Cedex 15, France.

The present invention also relates to a protein such as defined above which, in addition, has one or several of the following characteristics:

it is a glycoprotein;

its molecular weight, measured by electrophoresis on polyacrylamide gel, is 165,000 daltons.

The protein of the present invention has been isolated and characterized in the manner which will be described below, by preparation of hybrid cells capable of secreting antibodies which are characteristic of basal epidermal cells.

This protein is prepared by a method principally characterized by the fact that keratinocytes are used as starting materials, and, in particular, transformed human keratinocytes which can be cultivated in vitro; that a lysis of the cells is carried out with a suitable detergent; and that said protein is isolated in accordance with known methods for the purification of proteins, for example, a method comprising a step of affinity chromatography on a chromatographic support carried out with an antibody, such as described below.

The present invention also relates to antibodies capable of recognizing an antigen determinant of a protein defined above, which is present on the apicolateral surface of the wall of basal epidermal cells, in particular of the epidermis of man and other mammals such as those enumerated above. These antibodies are either monoclonal antibodies or polyclonal antibodies which are purified, for example, by immunoadsorption on the protein.

Among the monoclonal antibodies of the invention, those which are secreted by the hybrid cellular stock mentioned above can be cited in particular.

The present invention also relates to antibodies, as defined above, modified by marking with a radioactive, fluorescent or enzymatic tracer, obtained in accordance with conventional methods for preparing such marked antibodies.

For example, the tracer can be a radioactive tracer obtained by isotopic exchange with a radioactive isotope of iodine or indium.

The coupling of the antibodies with a fluorochrome (for example fluorescein or rhodamine isothiocyanate) or with an enzyme is also known. The enzyme is, for example, a peroxydase or an alkaline phosphatase. The enzyme activity possibly present on the reagent, after carrying out a test, can be determined using known methods with a suitable substrate providing, for example, an indication using colorimetry, fluorescence, luminescence, potentiometry, etc.

The present invention also relates to the antibodies obtained in accordance with the known technique of hybridomas starting from lymphocytes removed from immunized animals, using conventional methods, with the protein defined above.

The present invention further relates to the antibodies, as defined above, marked or not, fixed on a solid support enabling their use as immunoadsorbent agents in methods using affinity chromatography or as reagents in the methods of analysis based on the antigen-antibody reaction (radioimmunological techniques, immunofluorescence techniques and immunoenzymatic techniques).

The solid support can be prepared with any solid biological or synthetic material, having adsorbent properties or capable of fixing a coupling agent. These materials are known and described in the literature. Representative solid materials capable of fixing the antibodies by adsorption include, for instance, polystyrene, polypropylene, latex, etc. Representative solid materials which can be used to fix the antibodies by covalence using a coupling agent include dextran, cellulose, their amine derivatives (diethylaminoethyl cellulose or diethylaminoethyl dextran), etc.

The solid support can, for example, be in the form of discs, tubes, rods, bearings or microtitration plates.

The coupling agents enabling the antibodies to be fixed by covalence onto the solid support are bifunctional derivatives such as dialdehydes, quinones, etc.

The antibodies can also be fixed in a known manner onto solid mineral supports.

In order to prepare the monoclonal antibodies, hybrid cells are prepared in advance, and a further object of the invention is a method for the preparation of hybrid cells capable of secreting an antibody as defined above, wherein an animal is immunized with the protein defined above or with cells or cellular walls of a keratinocyte, in particular a human keratinocyte; the lymphocytes of the immunized animal are removed, using known methods; a cellular fusion is carried out with lymphocytes which can be cultivated in vitro; and a selection is made of the clones secreting antibodies capable of recognizing an antigen having the same characteristics as the protein defined above. The keratinocyte used as the starting material is, in particular, a keratinocyte transformed, for example, by the SV40 virus.

The present invention also relates to a method for the preparation of monoclonal antibodies by culture of the hybrid cellular stocks described above and separation of the antibodies produced in the culture medium or even in the ascites.

If desired, said antibodies are fixed on a support using known methods and/or are reacted with a radioactive, fluorescent or enzymatic marker in accordance with known methods.

The present invention also relates to the use of the monoclonal antibodies, such as are defined above, as reagents in techniques based on the antigen-antibody reaction.

These techniques, such as direct or indirect immunofluorescence, immunoenzymatic techniques, radioimmunological techniques, etc., are known and are not described herein.

The antibodies of the present invention can be used, in particular, as reagents for the study of the normal or pathological differentiation of epidermal cells. They can, in particular, be used in the diagnosis of dermatological diseases and also of diseases of the internal epithelia.

They also enable the determination of the presence of basal cells likely to constitute cancerous and/or residual lesional areas, for example after surgical treatment of a basocellular cancer.

They can be used in all medical imaging techniques using antibodies.

The antibodies of the present invention can also be used in flux cytometry to isolate the basal cells from a population of dermal cells treated with an appropriate dissociation agent (for example trypsin).

In addition, the antibodies of the present invention, fixed on an appropriate solid support, can be used in the preparation of reagents for affinity chromatography.

The following nonlimiting examples are given to illustrate the present invention.

EXAMPLE 1

Obtaining Monoclonal Antibodies

1) Culture of SV-K14 Cells

The stock of human keratinocytes transformed using the SV40 virus and called SV-K14 was used (Taylor-Papadimitriou et al, Cell Diff. 11, 169, 1982). This cell stock was deposited with ICRF (Imperial Cancer Research Fund, P.O. Box 123, Lincoln's Inn Fields, London WC2A3PX, U.K.).

The cells of this stock were cultured in an Eagle medium modified with Dulbecco containing 4.5 g/l of glucose and 1.2 g/l of sodium bicarbonate added to 10% calf fetal serum in a damp incubator containing 5% $CO_2$-95% air at 37° C. Appropriate tests enabled a check on the absence of mycoplasms in these cultures. Recent studies (Bernard et al, Cancer Res. 45, 1707, 1985) enabled it to be demonstrated that the SVK14 cells possess many characteristics of basal keratinocytes and are only capable of limited differentiation.

2) Immunization

Female BALB/c mice aged 8 to 12 weeks were immunized intraperitoneally with $2 \times 10^7$ SVK14 cells. This was repeated identically 3 weeks later. The animals' spleens were removed exactly 3 days after the second treatment.

3) Culture of SP2/0 Mouse Myeloma Cells

A stock of SP2/0 cells (Shulman and Köhler, Nature 276, 269, 1978) was used which are incapable of survival in a medium containing azaserine and hypoxanthine (Buttin et al, Curr. Top,. Microbiol. Immunol. 81, 27, 1978). The cells were cultured in an Eagle medium modified with Dulbecco (DME) containing 4.5 g/l of glucose, 1.2 g/l of sodium bicarbonate, 1 mM of sodium pyruvate, 2 mM of glutmine, 100 U of penicillin/ml, 1 $\mu$g of streptomycin/ml, (which is a complete DME medium) added to 10% decomplemented calf fetal serum (30 minutes at 56° C.). After thawing, the SP2/0 cells had to be cultured at concentrations from $2 \times 10^4$ to $5 \times 10^5$/ml until they doubled in a time of from 12 to 15 hours. The efficiency of cloning was determined by limit dilution and should be close to 100%. The freezing of these cells was carried out at a concentration of from $5 \times 10^6$ to $10^7$ ml in 95% calf fetal serum and 5% DMSO.

4) Preparation of SP2/0 Cells

SP2/0 cells in exponential growth at a concentration of $10^5$ to $2 \times 10^5$ cells per ml were centrifuged at 800 rpm for 5 minutes and resuspended in complete DME without serum at a density of $10^7$ cells/ml.

To carry out a fusion, $10^7$ myeloma cells are necessary.

5) Preparation of Splenocytes

The splenocytes of the immunized mice were prepared in a conventional manner and were placed in suspension in a complete DMEM (Dulbecco's Modified Essential Medium) medium without serum. For counting, 50 $\mu$l of the suspension were removed and mixed with 50 $\mu$l of 0.2% trypan blue and 400 $\mu$l of PBS (phosphate buffered saline). After 30 seconds, an aliquot was placed in a Buerker cell; the total number of splenocytes of a spleen was $10^8$ to $1.6 \times 10^8$. The percentage of dead cells was less than 20%. The suspension was centrifuged at 800 rpm for 5 minutes and adjusted to $10^8$ viable cells/ml.

6) Fusion (Day 0)

The technique used is derived from the technique of "fusion en masse" of Juy et al (J. Immunol. 129, 1153, 1982).

In a 50 ml polypropylene tube, $10^7$ myeloma cells (1 ml) and $4 \times 10^7$ splenocytes (0.4 ml) were mixed and centrifuged at 800 rpm (rotations per minute) for 5 minutes. The supernatant was pipetted, and 1 drop of complete DME was added without serum to the deposit which was then replaced in suspension (Galfre et al, Nature 266, 550, 1977). 400 μl of polyethylene glycol 1000 (PEG 1000) at 45% in the DME were added dropwise to the deposit over 30 seconds by slowly shaking the tube from time to time. It was left to react for 3 minutes at room temperature by slowly shaking from time to time. 1 ml of complete DME containing 10% of calf fetal serum (SFV) was then added over 5 minutes (approximately 1 drop every 2 seconds); the tube was inclined and lightly shaken. After these 5 minutes, 10 to 15 ml of complete medium containing calf fetal serum were rapidly added dropwise without shaking. This suspension was removed with a 10 ml pipette and distributed in a culture dish with a 100 mm diameter which was incubated in an incubator at 37° C. for 2 to 3 hours. Then the volume of the suspension was adjusted to 40 ml. The suspension was then distributed into the cups of culture plates with 24 holes at a rate of 0.4 ml/cup. 4 fusion plates were prepared.

7) Day 1

0.4 ml/cup of selective medium complete DME medium with SFV containing $5 \times 10^{-5}$M hypoxanthine and $10^{-5}$M azaserine was added.

8) Day 3

The operation of day 1 was repeated.

Under these conditions, hybridoma clones appeared between day 6 and day 9.

9) Marking the Clones Producing the Desired Antibodies

When the clones covered one-third of the surface of the cups and/or the medium became an orange yellow, the supernatant was tested using indirect immunofluorescence on SVK14 cultures and on epidermal sections in accordance with the techniques described by Bernard et al (Cancer Res. 45, 1707, 1985) and Bernard et al (Brit. J. Dermatol. 112, 617, 1985).

10) Transplanting Selected Cups

Before the cups were half full, they were transplanted into 3 other cups in total. At this stage were carried out, on the one hand, a freezing and, on the other hand, a subcloning into plates with 96 holes (1 row with 10 cells/cup, 1 row with 5 cells/cup, 2 rows with 2 cells/cup, 2 rows with 1 cell/cup, 2 rows with 0.5 cell/cup). For the subcloning a plate containing a medium composed of 20 to 50% of macrophage supernatant could also be prepared. The supernatants of the positive cups were tested using indirect immunofluorescence. Two positive clones were then cultured.

One of the two clones ($BC_2$) was deposited in the National Collection of the Pasteur Institute, under the number previously indicated.

11) Growth in Ascite

The growth of a hybridoma in ascite liquid was obtained after intraperitoneal injection of $10^7$ cells from a same clone to BALB/c mice aged 8 weeks which had been previously sensitized by intraperitoneal injection of 0.5 ml of pristane (pristane is 2,6,10,14-tetramethyl pentadecane).

12) Identification of the Class and Subclass of Secreted Immunoglobulins

The class of the immunoglobulins secreted in the myeloma supernatant was determined by double diffusion in agar with specific reagents of the heavy chains of immunoglobulins (Serotec Ltd., Bicester, Great Britain).

The immunoglobulin secreted by the $BC_2$ clone was an IgG1.

EXAMPLE 2

Identification of Recognized Antigens

1) SVK14 Cell

Studies carried out using indirect immunofluorescence have shown that the immunoglobulin secreted by the $BC_2$ cell enabled considerable marking of the unfixed SVK14 cells, of those fixed with formaldehyde, and those fixed with formaldehyde in the presence of Triton X-100 (isooctylphenol polyethyloxylated with 10 moles of ethylene oxide).

2) Immunoprecipitation

The SVK14 cells were metabolically marked for 24 hours at 37° C. with $^{35}$S-methionine or 2-$^3$H-mannose, in a complete culture medium. The medium contained 150 μCi of $^{35}$S-methionine (New England Nuclear; 400 Ci/mmol) for 100 μCi of 2-$^3$H-mannose (New England Nuclear; 20 Ci/mmol) per ml. After washing with PBS, the cells were lysed on ice and for 30 minutes in an extraction buffer composed of PBS without $CA^{++}$ or $Mg^{++}$, containing 1% of Triton X-100, 0.5% of sodium deoxycholate, 0.1% of sodium dodecylsulfate and 0.2% of $NaN_3$. This buffer further contained 25 μl of DNAse I (at 2 mg/ml) and 5 μl RNAse A (at 5 mg/ml). 10 ml of lysis buffer were necessary to lyse 175 $cm^2$ of cultures. The supernatants were collected and clarified by centrifugation at 15,000 g for 30 minutes at 4° C. The immunoprecipitation was carried out by incubating 500 μl of cellular extract with 3 μl of supernatant from the hybridoma culture medium for 16 hours at 4° C. Then, 50 μl of rabbit immunoglobulins mouse anti-immunoglobulin (Cappel Laboratories, Cochranville, Pa., USA) were added and the incubation was extended for 2 hours at 4° C. The immune complexes were then isolated by adding 150 μl of A-Sepharose protein (Pharmacia Fine Chemicals, Uppsala, Sweden) diluted in 500 μl of lysis buffer, incubating it while stirring for 2 hours at 20° C. and centrifuging it at 13,000 g for 10 minutes. After 3 washes in the lysis buffer, the deposit was extracted at 100° C. in the presence of 1% sodium dodecylsulfate (SDS) at 5% betamercaptoethanol and analyzed by electrophoresis in polyacrylamide-SDS gel using the method of Laemmli (Laemmli, Nature, 277, 680, 1970).

In this manner, the protein of the invention was obtained which had the characteristics mentioned above.

3) Immunodetection After Electrotransfer of Proteins

The technique used is similar to that described by Bernard et al (Cancer Research 45, 1707, 1985). The SVK14 cells were lysed in PBS containing 1% sodium dodecylsulfate and 5% betamercaptoethanol. After scratching the culture dishes, the extracts were clarified by sonication and heating to 100° C. for 5 minutes. The cellular proteins (60 μl in 20 μl) were then separated by electrophoresis in polyacrylamide-SDS gel and transferred onto nitrocellulose using the method of Towbin et al (Proc. Natl. Acad. Sci. USA 76, 4350, 1979). The reactive protein bands (that is reacting with the antibody) were then shown by the technique of coloration using peroxydase described by Glass et al (Science 211, 70, 1980).

4) Specificity of the Organic Tissues

The specificity of the antibodies present in the myeloma supernatants and the ascite liquids was studied using indirect immunofluorescence on frozen sections of 4 μm in thickness as described by Bernard et al (Brit. J. Dermatol. 112, 647, 1985). Epithelial tissues of varied animal origins were used so as to study the specificity of each species, and the various epithelial tissues of human origin were used to study the specificity of the organic tissues. Human pathological tissues were also used to evaluate the diagnostic value of the present invention. This study related to the pathological skins of benign tumors, malignant tumors and dermatoses associated with anomalies of proliferation and keratinocytic differentiation.

5) Reactivity of the Antibodies with the Antigens with a Cellular Surface

When, during indirect immunofluorescence on a frozen section of nonpathological human skin, the marking appears membranous, this localization was confirmed by immunomarking using an electronic microscope employing the method of Graham and Karnovsky (J. Histochem. Cytochem. 14, 291, 1966), by immunomarking of cells in culture, fixed with paraformaldehyde (PFA) diluted to 3% in PBS (Bernard et al, Cancer Res. 45, 1707, 1985), and by immunomarking on isolated cells by careful trypsination from human epidermis (Freeman et al, In Vitro 12, 352, 1976).

6) Results

These studies have enabled an antigen system localized at the level of the apicolateral surfaces of the basal epidermal cell to be defined.

The antibody ($BC_2$) capable of recognizing this antigen is secreted by the hybrid stock obtained as described above.

The antibody ($BC_2$) identifies a glycoprotein of 165,000 daltons. This protein was immunoprecipitated by $BC_2$ from a cellular extract of SVK14 cells marked with $^{35}S$-methonine and with $2$-$^3H$-mannose. Immunofluorescence and electronic microscope studies demonstrated the polarized distribution of this antigen on the surface of the basal cells of the human skin. This antigen has been detected in man, monkey, horse, cow, goat, and guinea pig, but not in rabbit and mouse. In all cases, the polarized distribution was observed. It was retained on the human keratinocytes after dissociation using trypsin. The marking was detected by indirect immunofluorescence on the surface of SVK14 cells in culture (i) fixed with paraformaldehyde and permeabilized or not with Triton X-100 (Bernard et al, Cancer Res. 45, 1707, 1985) and (ii) fixed with methanol at −20° C. (ibid.). The distribution of this antigen was not altered in the case of hyperproliferative diseases of the skin such as psoriasis or papilloma.

The antigen was also present, particularly, in the case of basocellular carcinoma. It was absent in the cases of melanoma and naevus. The results obtained are summarized in Tables I and III below:

TABLE I
SPECIES SPECIFICITY OF THE ANTIBODY SECRETED BY THE $BC_2$ CELL

| Species Tested[a] | | | | | | | |
|---|---|---|---|---|---|---|---|
| Mouse | Rabbit | Guinea Pig | Goat | Cow | Horse | Monkey | Man |
| − | − | ++ | + | ++ | + | ++ | +++ |

[a] by immunofluorescence on frozen sections of skin
+++ considerable marking
++ less considerable marking
+ weak marking
− marking absent

TABLE II
SPECIFICITY OF THE ORGANIC TISSUE IN MAN OF THE ANTIBODY SECRETED BY $BC_2$

| Tissues Tested[a] | | | | | |
|---|---|---|---|---|---|
| Skin | Esophagus | Ureter | Stomach | Colon | Small Intestine |
| ++ | ++ | ++ | + | + | + |

[a] by immunofluorescence on frozen sections of skin

TABLE III
CUTANEOUS PATHOLOGY: ABSENCE OR PRESENCE OF THE ANTIGEN RECOGNIZED BY THE ANTIBODY SECRETED BY $BC_2$

| Melanoma (5)[a] | Naevus (2) Naevus (2) | Basocellular Carcinoma (4) | Spinocellular Carcinoma (4) |
|---|---|---|---|
| − | − | ++ (intestines) | + (intestines) − (horned balls) |

[a] The figure in parentheses represents the number of cases studied.

We claim:

1. A protein, characterized by the fact:
   that it is a nonkeratinic protein present on the apicolateral surface and absent on the basal surface of basal epidermal cells in man, monkey, horse, cow, goat and guinea pig, including psoriasic and papillomatous basal cells;
   that is absent from the surface of the basal epidermal cells in the rabbit and the mouse;
   that it is present in the following epithelial tissues in man, in addition to the skin: esophagus, ureter and, to a lesser degree, stomach, colon and small intestine;
   that it is present in a non polarized manner on the following pathological cells: basocellular carcinoma, spinocellular carcinoma, and absent on the melanoma and naevus cells;
   that it is recognized by the antibody secreted by the hybrid cellular stock $BC_2$ deposited on Oct. 27, 1986 in the National Collection of Microorganisms of the Pasteur Institute under the No. I-614;
   that it is a glycoprotein;
   that it has a molecular weight of about 165,000 daltons as determined by sodium dodecyl sulphate polyacrylamide gel electrophoresis under reducing conditions; and
   that it is purified and isolated from other basal epidermal cell materials which do not bind to said antibody.

2. An antibody characterized by the fact that it recognizes an antigen determinant of a protein defined in claim 1, said antibody being a monoclonal antibody or a purified polyclonal antibody.

3. The antibody of claim 2 which is secreted by the hybrid cellular stock $BC_2$.

4. The antibody of claim 2 which is marked.

5. The antibody of claim 2 which is fixed on a solid support.

6. The antibody of claim 2 which is marked and fixed on a solid support.

7. Hybrid cellular stock that secretes an antibody defined in claim 2.

* * * * *